United States Patent
de Villeneuve et al.

(10) Patent No.: US 9,816,059 B2
(45) Date of Patent: *Nov. 14, 2017

(54) STABILIZED CAPSULE COMPOSITIONS

(71) Applicant: International Flavors & Fragrances Inc., New York, NY (US)

(72) Inventors: Volkert de Villeneuve, Voorburg (NL); Djurre Sijbren Postma, Zeewolde (NL); Elizabeth Geertruida Maria Brundel, Nijkerk (NL); John Brahms, Morris Plains, NJ (US); Li Xu, Edison, NJ (US); Joan G. L. Pluter, Middletown, NJ (US); Laura French, Jersey City, NJ (US); Yabin Lei, Holmdel, NJ (US); Lewis Michael Popplewell, Morganville, NJ (US); Xiao Huang, Freehold, NJ (US)

(73) Assignee: INTERNATIONAL FLAVORS & FRAGRANCES, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,342

(22) Filed: Dec. 22, 2014

(65) Prior Publication Data

US 2015/0252312 A1 Sep. 10, 2015

Related U.S. Application Data

(63) Continuation-in-part of application No. 13/967,800, filed on Aug. 15, 2013, now abandoned, and a continuation-in-part of application No. 13/968,862, filed on Aug. 16, 2013, and a continuation-in-part of application No. 13/969,038, filed on Aug. 16, 2013, now Pat. No. 9,687,424, and a continuation-in-part of application No. 13/163,320, filed on Jun. 17, 2011, and a continuation-in-part of application No. 12/883,337, filed on Sep. 16, 2010, now abandoned, and a continuation-in-part of application No. 12/562,578, filed on Sep. 18, 2009, now Pat. No. 8,299,011.

(51) Int. Cl.
| | | |
|---|---|---|
| *C11D 17/00* | (2006.01) | |
| *C11B 9/00* | (2006.01) | |
| *C11D 3/00* | (2006.01) | |
| *C11D 3/37* | (2006.01) | |
| *A61K 8/73* | (2006.01) | |
| *A61K 8/84* | (2006.01) | |
| *A61K 8/11* | (2006.01) | |
| *B01J 13/14* | (2006.01) | |
| *B01J 13/16* | (2006.01) | |
| *B01J 13/20* | (2006.01) | |
| *C11D 3/50* | (2006.01) | |
| *A61Q 13/00* | (2006.01) | |
| *A23L 27/00* | (2016.01) | |

(52) U.S. Cl.
CPC .......... *C11D 17/0039* (2013.01); *A23L 27/72* (2016.08); *A23L 27/74* (2016.08); *A61K 8/11* (2013.01); *A61K 8/731* (2013.01); *A61K 8/84* (2013.01); *A61Q 13/00* (2013.01); *B01J 13/14* (2013.01); *B01J 13/16* (2013.01); *B01J 13/206* (2013.01); *C11B 9/00* (2013.01); *C11D 3/0015* (2013.01); *C11D 3/505* (2013.01); *A61K 2800/412* (2013.01); *A61K 2800/624* (2013.01); *C11D 3/3726* (2013.01)

(58) Field of Classification Search
CPC ... C11D 17/0039; C11D 3/001; C11D 3/3726; C11D 3/505; C11B 9/00; A61Q 5/12; A61K 8/731; A61K 8/11; A61K 8/84; A61K 2800/624; A61K 2800/412; B01J 13/14; B01J 13/16; B01J 13/206
See application file for complete search history.

(56) References Cited

U.S. PATENT DOCUMENTS

| | | | |
|---|---|---|---|
| 3,743,601 A | 7/1973 | Schnoring et al. | |
| 3,963,680 A | 6/1976 | O'Keefe et al. | |
| 4,280,833 A | 7/1981 | Beestman et al. | |
| 4,563,212 A | 1/1986 | Becher et al. | |

(Continued)

FOREIGN PATENT DOCUMENTS

| | | |
|---|---|---|
| EP | 1693104 A1 | 8/2006 |
| JP | 5068970 A | 6/1975 |

(Continued)

OTHER PUBLICATIONS

Dow Plastics—"PAPI 135". Retrieved on Jan. 3, 2017. Retrieved from the internet <URL: http://msdssearch.dow.com/PublishedliteratureDOWCOM/dh_003f/0901b8038003f163.pdf>.

(Continued)

*Primary Examiner* — Anoop Singh
*Assistant Examiner* — Doan Phan
(74) *Attorney, Agent, or Firm* — Martin Zhang; XuFan Tseng; Elizabeth M. Stiver

(57) ABSTRACT

A capsule composition containing a capsule and a stabilizing agent. The capsule has an oil core containing an active material and a capsule wall encapsulating the oil core. The active material is a fragrance, a flavor, a malodor counteractant, or a combination thereof. The wall is formed of polyurea or polyurethane. The capsule composition has 20 ppm or greater of the stabilizing agent, which is a multifunctional amine, an amino acid, a polymer mixture, or a combination thereof. Also disclosed is a consumer product containing this capsule composition.

20 Claims, No Drawings

(56) References Cited

U.S. PATENT DOCUMENTS

| | | |
|---|---|---|
| 4,640,709 A | 2/1987 | Beestman |
| 4,785,048 A | 11/1988 | Chao et al. |
| 4,798,862 A | 1/1989 | Gillis et al. |
| 5,164,126 A | 11/1992 | Kalishek et al. |
| 5,304,448 A | 4/1994 | Keoshkerian et al. |
| 5,324,584 A | 6/1994 | Juang et al. |
| 5,635,211 A | 6/1997 | Nehen et al. |
| 5,705,174 A | 1/1998 | Benoff et al. |
| 5,866,153 A | 2/1999 | Hasslin et al. |
| 5,925,595 A | 7/1999 | Seitz et al. |
| 6,133,197 A | 10/2000 | Chen et al. |
| 6,340,653 B1 | 1/2002 | Scher et al. |
| 6,586,107 B2 | 7/2003 | Klug et al. |
| 6,797,670 B2 | 9/2004 | Kleban et al. |
| 7,125,835 B2 | 10/2006 | Bennett et al. |
| 7,632,789 B2 | 12/2009 | Brain et al. |
| 8,026,206 B2 | 9/2011 | Sajic et al. |
| 8,299,011 B2 | 10/2012 | Lei et al. |
| 2002/0079599 A1 | 6/2002 | Kleban et al. |
| 2004/0121155 A1 | 6/2004 | Matsunami et al. |
| 2004/0156742 A1 | 8/2004 | Milan et al. |
| 2005/0153135 A1 | 7/2005 | Popplewell et al. |
| 2005/0153839 A1 | 7/2005 | Tamura et al. |
| 2005/0161843 A1 | 7/2005 | Wang et al. |
| 2005/0271735 A1 | 12/2005 | Stover et al. |
| 2007/0042182 A1* | 2/2007 | Markus ................ A01N 65/00 428/402.2 |
| 2007/0138672 A1 | 6/2007 | Lee et al. |
| 2007/0202063 A1 | 8/2007 | Dihora et al. |
| 2008/0103265 A1 | 5/2008 | Schocker et al. |
| 2008/0131695 A1 | 6/2008 | Aouad et al. |
| 2008/0187596 A1 | 8/2008 | Dihora et al. |
| 2008/0200363 A1 | 8/2008 | Smets et al. |
| 2008/0206291 A1 | 8/2008 | Ouali et al. |
| 2010/0009893 A1 | 1/2010 | Cavin et al. |
| 2010/0086575 A1* | 4/2010 | Dihora ................... A61K 8/11 424/401 |
| 2010/0119679 A1* | 5/2010 | Dihora ................... B01J 13/16 426/534 |
| 2011/0077188 A1 | 3/2011 | Ouali et al. |
| 2011/0077375 A1* | 3/2011 | Kulke ................ C08G 18/8064 528/45 |
| 2011/0230390 A1 | 9/2011 | Ouali et al. |
| 2012/0016139 A1 | 1/2012 | Screen et al. |
| 2012/0148644 A1 | 6/2012 | Popplewell et al. |
| 2013/0109569 A1 | 5/2013 | Dave et al. |
| 2013/0330292 A1 | 12/2013 | Lei et al. |
| 2013/0337023 A1 | 12/2013 | Lei et al. |
| 2014/0017287 A1 | 1/2014 | Lei et al. |

FOREIGN PATENT DOCUMENTS

| | | | |
|---|---|---|---|
| WO | 2004098767 A1 | 11/2004 | |
| WO | 2006006003 A1 | 1/2006 | |
| WO | 2007137441 A1 | 12/2007 | |
| WO | WO 2008031241 A1 * | 3/2008 | ............ B01J 13/14 |
| WO | WO 2009091726 A1 * | 7/2009 | ............ A61K 8/11 |
| WO | 2009103615 A1 | 8/2009 | |
| WO | WO 2011154893 A1 * | 12/2011 | ............ B01J 13/16 |
| WO | 2012107323 A1 | 8/2012 | |
| WO | 2013000587 A1 | 1/2013 | |
| WO | 2013059167 A2 | 4/2013 | |
| WO | 2013092958 A1 | 6/2013 | |

OTHER PUBLICATIONS

Chinese First Office Action dated Jan. 30, 2014 for Application No. CN 201010548980.0(with English Translation included).

Office Communication dated Oct. 18, 2011 from U.S. Appl. No. 12/562,578, filed Sep. 18, 2009.

Office Communication dated Aug. 21, 2012 from U.S. Appl. No. 13/163,320, filed Jun. 17, 2011.

Office Communication dated Nov. 21, 2012 from U.S. Appl. No. 13/163,320, filed Jun. 17, 2011.

* cited by examiner

STABILIZED CAPSULE COMPOSITIONS

CROSS-REFERENCE TO RELATED APPLICATIONS

This application claims priority to International Application PCT/US14/51309, filed Aug. 15, 2014, and four U.S. patent applications, Ser. Nos. 13/967,800, 13/968,862, 13/969,038, and 13/163,320. The first three U.S. patent applications were filed on Aug. 16, 2013. The last was filed on Jun. 17, 2011. International Application PCT/US14/51309 is a continuation in part of U.S. application Ser. Nos. 13/967,800, 13/968,862, and 13/969,038, each of which is a continuation-in-part of U.S. patent application Ser. No. 13/163,320, filed on Jun. 17, 2011, which is a continuation-in-part of U.S. patent application Ser. No. 12/883,337, filed on Sep. 16, 2010, now abandoned, which is a continuation-in-part of U.S. patent application Ser. No. 12/562,578, filed on Sep. 18, 2009, now U.S. Pat. No. 8,299,011. The contents of the above-mentioned applications are incorporated herein by reference in their entirety.

BACKGROUND

Nano- or micro-encapsulation is used in a variety of different applications where there is a need to deliver, apply, or release an active material including a fragrance, flavor, and malodor counteraction agent to a target area in a time-delayed or controlled manner. Various techniques for preparing capsules are known in the art and are used, depending on the contents to be encapsulated, the environment in which the capsules should retain their integrity and the desired release mechanism.

Interfacial polycondensation is a known technique for preparing capsules and versatile capsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water-immiscible and includes a polyfunctional isocyanate, i.e., a polyisocyanate having two or more isocyanate groups, and a second aqueous phase which includes (i) a polyfunctional alcohol (i.e., a polyol) having two or more —OH groups, or (ii) a polyfunctional amine (i.e., a polyamine) having two or more —NH$_2$ and/or —NH groups.

If the active material to be encapsulated is hydrophobic, it will be included in the water-immiscible phase (i.e., the oil phase), thereafter the oil phase are mixed with a water phase by high shear mixing to form an oil-in-water emulsion. In this emulsion, the polycondensation reaction will take place. Thus, the small droplets of the oil phase will be surrounded by the capsule wall formed by polycondensation of the isocyanate and the polyalcohol or polyamine as starting materials. Conversely, if the material to be encapsulated is hydrophilic, it will be included in the water phase and the mixture of the water and oil phases converted into a water-in-oil emulsion. The polycondensation reaction will then form capsule walls surrounding the droplets of water phase. Suitable emulsifiers are often utilized to aid in the preparation and stabilization of the emulsion.

Raw materials and processes for preparing capsules by polycondensation are described in U.S. Pat. No. 4,640,709 and the publications described therein. As is exemplified therein, and also in U.S. Pat. No. 6,133,197, polyurea and polyurethane capsules are often used for rugged applications, such as for encapsulation of agrochemicals, e.g., herbicides and pesticides, where slow time-release is desired to set the agents free. For such applications, the capsules also require a relatively high mechanical strength. For the polycondensation reaction, suitable diisocyanate and symmetrical triisocyanate starting materials are disclosed in the prior art.

WO 2011/154893 discloses a process for the preparation of capsules, which includes mixing at least one aliphatic polyisocyanate and of at least one aromatic polyisocyanate, wherein the molar ratio between the two polyisocyanates is between 75:25 and 20:80.

WO 2013/000587 discloses a process for the preparation of polyurea capsules, which includes dissolving at least one polyisocyanate having at least two isocyanate functional groups, in a perfume to form a solution; adding to the solution an aqueous solution of an emulsifier or of a colloidal stabilizer; and adding to the mixture to 3,5-diamino-1,2,4-triazole to form a polyurea wall.

U.S. Pat. No. 5,304,448 describes an encapsulated toner composition using reaction of amino acids and polyisocyanates.

Known polyurea or polyurethane capsules face various issues, e.g., low olfactory intensity and low stability, and high toxicity. Their deposition to target surfaces is also problematic.

There is a need to develop a safe, stable, and high efficient capsules for use in laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is based on the discovery that certain capsule compositions possess unexpected desirable properties including great stability.

Accordingly, one aspect of this invention relates to a capsule composition comprising a capsule that has an oil core containing an active material and a capsule wall encapsulating the oil core, and a stabilizing agent. In this composition, the active material is a fragrance, a flavor, a malodor counteractant, or a combination thereof (preferably a fragrance); the wall is formed of polyurea or polyurethane; and the stabilizing agent is a multi-functional amine, an amino acid, a polymer mixture, or a combination thereof, the polymer mixture containing a first polymer selected from the group consisting of polyvinylpyrrolidone, polyvinylpyridine-N-oxide, polylysine, and polyvinyl imidazolinium, and a second polymer.

Examples of a stabilizing agent include hexamethylene diamine, hexaethylenediamine, ethylenediamine, 1,3-diamino-propane, 1,4-diamino-butane, diethylenetriamine, pentaethylenehexamine, bis(3-amino-propyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, and a combination thereof. Preferably, the polyfunctional amine is hexamethylene diamine, 1,3-diaminoguanidine, 1,1-dimethylbiguanide, guanidine, arginine, lysine, or a combination thereof. Preferably, the stabilizing agent is hexamethylenediamine, amino-2-methyl-1-propanol, lysine, arginine, histidine, or a combination thereof.

The content of the stabilizing agent is 20 ppm or greater (e.g., 20 ppm to 2%, 50 ppm to 1%, and 50 to 2000 ppm) by the weight of the capsule composition.

Polyurea as a capsule wall material is typically a reaction product of a polyfunctional isocyanate and a polyfunctional amine as a cross-linking agent in the presence of a capsule formation aid. The polyfunctional isocyanate can be an aromatic polyfunctional isocyanate, aliphatic polyfunctional isocyanate, or combination thereof. Suitable aromatic polyfunctional isocyanates include those containing a phenyl, tolyl, xylyl, naphthyl, or diphenyl moiety, or a combination thereof. Examples are polyisocyanates of toluene diisocyanate, trimethylol propane-adducts of toluene diisocyanate, trimethylol propane-adducts of xylylene diisocyanate, polymeric methylene diphenyl diisocyanate, methylene diphenyl diisocyanate, and a combination thereof. Suitable aliphatic polyfunctional isocyanate include trimers of hexamethylene diisocyanate, trimers of isophorone diisocyanate, biurets of hexamethylene diisocyanate, hydrogenated polymeric methylene diphenyl diisocyanate, hydrogenated methylene diphenyl diisocyanate, and a combination thereof. Examples of the polyfunctional amine include hexamethylene diamine, hexaethylenediamine, ethylenediamine, 1,3-diamino-propane, 1,4-diamino-butane, diethylenetriamine, pentaethylenehexamine, bis(3-amino-propyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, and a combination thereof. Preferably, the polyfunctional amine is hexamethylene diamine, 1,3-diaminoguanidine, 1,1-dimethylbiguanide, guanidine, arginine, lysine, or a combination thereof. Suitable capsule formation aids include polyvinyl alcohol, polystyrene sulfonate, carboxymethyl cellulose, naphthalene sulfonate, polyvinylpyrrolidone, copolymers of vinyl pyrrolidone and quaternized dimethylaminoethyl methacrylate, and any mixture thereof. More exemplary capsule formation aids are mixtures of carboxymethyl cellulose and polystyrene sulfonate, mixtures of carboxymethyl cellulose and polyvinylpyrrolidone, and mixtures of polyvilypyrrolidone and a copolymer of vinyl pyrrolidone and quaternized dimethylaminoethyl methacrylate.

Another suitable capsule wall material is polyurethane, which can be a reaction product of a polyfunctional isocyanate and a polyfunctional alcohol as a cross-linking agent in the presence of a capsule formation aid.

Any capsule composition described above can further contain a deposition aid that is an anionic, cationic, nonionic or zwitterionic polymer. Examples include polyquaternium-6, polyquaternium-47, polyquaternium-53, polyvinylamine, poly(vinsylamine-co-vinylformamide), and any combination thereof (e.g., a combination of polyquaternium-6 and polyvinylamine, and a combination of polyquaternium-47 and polyvinylamine).

In any of the capsule compositions described above, the oil core can be 35 to 99.9% (e.g., 50 to 98%) and by weight of the capsule and the capsule wall is 0.1 to 65% (e.g., 2 to 50%) by weight of the capsule.

The capsule, before formulating into the capsule composition, can be purified by washing the capsule with water or an aqueous solution, and/or be cured at a temperature of 55° C. or greater.

Another aspect of this invention relates to a consumer product containing one of the capsule compositions described above. The consumer product can be a shampoo, a hair conditioner, a soap, a body wash, a cosmetic preparation, an all-purpose cleaner, a fabric softener, a fabric refresher, an ironing water, a fabric detergent, a unit dose tablet or capsule, a scent booster, a drier sheet, a fine fragrance, an Eau De Toilette product, a deodorant, an anti-perspirant, an roll-on product, or an aerosol product. Preferably, the consumer product is a fabric softener containing 1 to 30% of a fabric softening agent, 0.1 to 30% of the capsule, and 50 ppm to 1% of the stabilizing agent. A more preferably embodiment is a fabric softener containing 2 to 20% of a fabric softening agent and 50 to 2000 ppm of hexamethylenediamine as the stabilizing agent.

The details of one or more embodiments of the invention are set forth in the description below. Other features, objects, and advantages of the invention will be apparent from the description and the claims.

DETAILED DESCRIPTION OF THE INVENTION

It has been found that polyurea/polyurethane capsule compositions prepared with a polyisocyanate and a cross-linking agent are suitable for carrying various kinds of hydrophobic or hydrophilic active materials of use in products intended for application to animate and inanimate surfaces.

Polyurea/polyurethane capsule compositions of this invention are useful in a wide range of consumer applications, e.g., personal care products including shampoo, hair conditioners, personal wash such as soaps, body wash, personal cleaners and sanitizers, fabric care such as fabric refreshers, softeners and dryer sheets, ironing water, industrial cleaners, liquid and powder detergent including unit dose capsules, rinse conditioners, scent booster products, fine fragrances, an Eau De Toilette product, a deodorant, an roll-on product, or an aerosol product.

More specifically, the capsule compositions of this invention are well-suited for use in fabric softeners. Moreover, the inclusion of a stability agent provides fabric softeners with excellent storage stability of viscosity and retention of an encapsulated fragrance.

Certain capsules useful in this invention are prepared from anionic capsule formation aids and have a positive zeta-potential of 5 mV to 200 mV (e.g., 20-80 mV), which provides strong affinity to specific animate and inanimate surfaces.

Suitable capsules can be prepared by reacting a polyisocyanate with a cross-linking agent in the presence of a capsule formation aid (e.g., a dispersant) and/or a catalyst (e.g., a base) so that an active material is encapsulated in an oil core by a capsule wall. The oil core optionally contains a core modifier.

These capsule-forming materials are described in detail below.

Polyisocyanate. The polyurea or polyurethane capsules of this invention are prepared using one or more polyisocyanates. Each of them has two or more isocyanate groups, i.e., O=C=N—, wherein said polyisocyanate can be aromatic, aliphatic, linear, branched, or cyclic. In certain embodiments, the polyisocyanate contains, on average, 2 to 4 —N=C=O groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

In other embodiments, the polyisocyanate is an aliphatic polyisocyanate. In certain embodiments, the aliphatic polyisocyanate is a trimer of hexamethylene diisocyanate, a trimer of isophorone diisocyanate or a biuret of hexamethylene diisocyanate. Exemplary aliphatic polyisocyanates include those commercially available, e.g., BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation, Pittsburgh, Pa.).

One class of suitable polyisocyanates are aromatic polyisocyanates that have the generic structure below, and its structural isomers

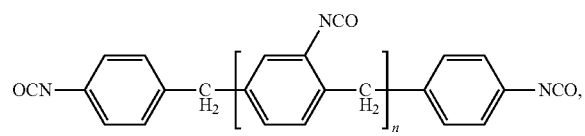

wherein n can vary from zero to a desired number depending on the type of polyamine or polyol used. For the purpose of this invention, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5.

Specific examples of wall monomer isocyanates include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Other suitable commercially-available polyisocyanates include LUPRANATE M20 (polymeric methylene diphenyl diisocyanate, "PMDI" commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Bayer), and TAKENATE D110-N (xylene diisocyanate adduct polymer commercially available from Mitsui Chemicals corporation, Rye Brook, N.Y., containing NCO 11.5 wt %).

In particular embodiments, an exemplary polyisocyanate has the following structure:

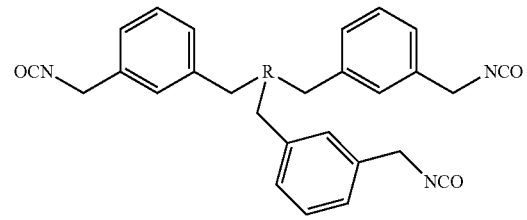

or its structural isomer. Representative polyisocyanates are TAKENATE D-110N (a polyisocyanate based on xylene diisocyanate commercially available from Mitsui), DESMODUR L75 (a polyisocyanate base on toluene diisocyanate commercially available from Bayer), and DESMODUR IL (another polyisocyanate based on toluene diisocyanate commercially available from Bayer).

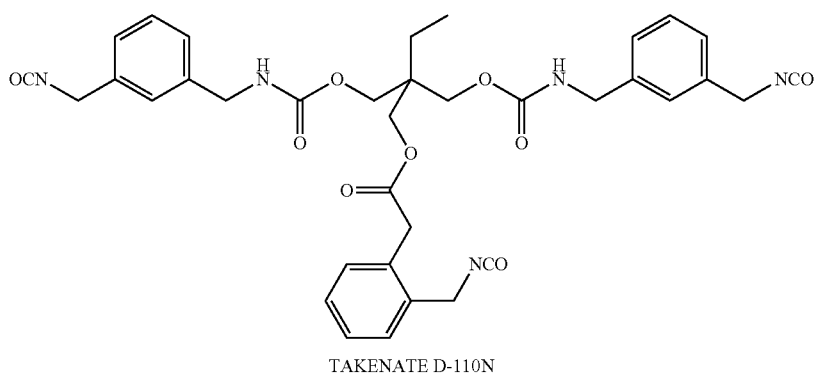

TAKENATE D-110N

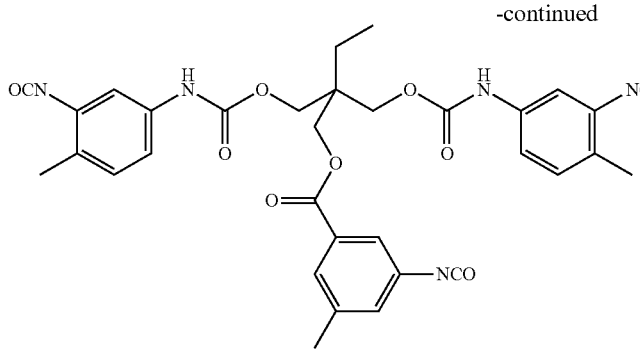

DESMODUR L75

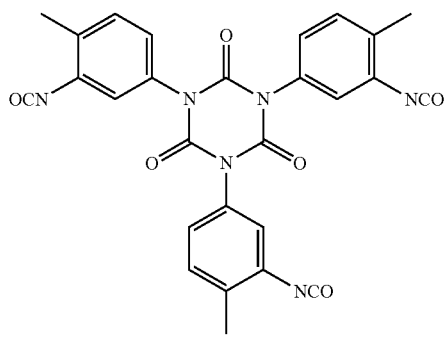

DESMODUR IL

In some embodiments, the polyisocyanate used in the preparation of the polyurea or polyurethane capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea compositions of this invention.

The average molecular weight of certain polyisocyanates useful in this invention varies from 250 to 1000 Da and preferable from 275 to 500 Da. In general, the range of the polyisocyanate concentration in the composition of this invention varies from 0.1% to 10%, preferably from 0.1% to 8%, more preferably from 0.2 to 5%, and even more preferably from 1.5% to 3.5%, all based on the total capsule composition.

More examples of suitable isocyanates can be found in PCT 2004/054362; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

Cross-Linking Agent. Cross-linking agents are used to form the capsule walls. These agents in general contains multiple (i.e., two or more) function groups (e.g., —NH—, —NH$_2$ and —OH) that can react with polyisocyanates to form polyureas or polyurethanes. Examples include multi-functional amines (e.g., polyamines) and multi-functional alcohols (e.g., polyols).

Suitable polyamines contain two or more amine groups including —NH$_2$ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl.

Two classes of such polyamines include polyalkylene polyamines having the following structures:

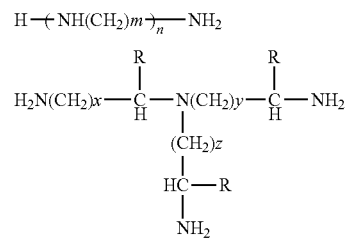

In which R is hydrogen or —CH$_3$; and m, n, x, y, and z each are integers from 0-2000 (e.g., 1, 2, 3, 4, and 5). Examples include ethylene diamine, 1,3-diaminepropane, diethylene triamine, triethylene tetramine, 1,4-diaminobutane, hexaethylene diamine, hexamethylene diamine, pentaethylenehexamine, and the like.

Another class of polyamines are polyalykylene polyamines of the type:

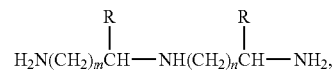

where R equals hydrogen or —CH$_3$, m is 1-5 and n is 1-5, e.g., diethylene triamine, triethylene tetraamine and the like. Exemplary amines of this type also include diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

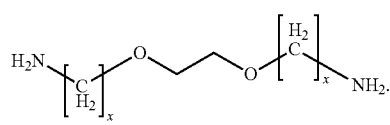

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 having a structure shown above (where $x=2$), JEFFAMINE EDR-176 (where $x=3$) (from Huntsman). Other polyether amines include the JEFFAMINE ED Series, JEFFAMINE TRIAMINES, polyethylenimines from BASF (Ludwigshafen, Germany) under LUPASOL grades (e.g., Lupasol FG, Lupasol G20 waterfree, Lupasol PR 8515, Lupasol WF, Lupasol FC, Lupasol G20, Lupasol G35, Lupasol G100, Lupasol G500, Lupasol HF, Lupasol PS, Lupasol HEO 1, Lupasol PN50, Lupasol PN60, Lupasol P0100 and Lupasol SK). Other commercially available polyethylenimines include EPOMIN P-1000, EPOMIN P-1050, EPOMIN RP18W and EPOMIN PP-061 from NIPPON SHOKUBAI (New York, N.Y.). Polyvinylamines such as those sold by BASF under LUPAMINE grades can also be used. A wide range of polyetheramines may be selected by those skilled in the art. In certain embodiments, the cross-linking agent is hexamethylene diamine, polyetheramine or a mixture thereof.

The structures of specific cross-linking agents are shown in the table below:

 Diethylenetriamine
 Tris(2-aminoethyl)amine
H(NHCH$_2$CH$_2$)$_5$NH$_2$
Pentaethylenehexamine
 Bis(3-aminopropyl)amine
 Bis(hexanethylene)triamine
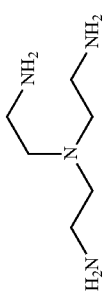 Triethylenetetramine
 1,3-Diaminoguanidine monohydrochloride
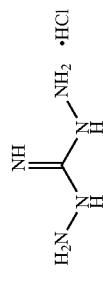 N,N'-Bis(3-aminopropyl)-1,3-propanediamine -continued
Tetraethylenepentamine
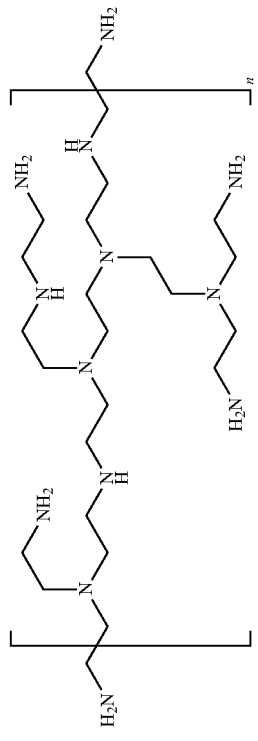
Branched Polyethylenimine
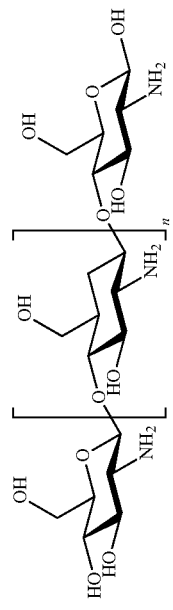
Chitosan
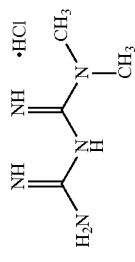
1,1-Dimethylbiguanide hydrochloride
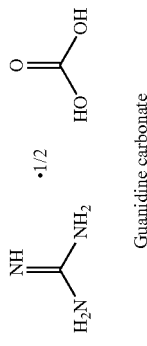
Guanidine carbonate -continued
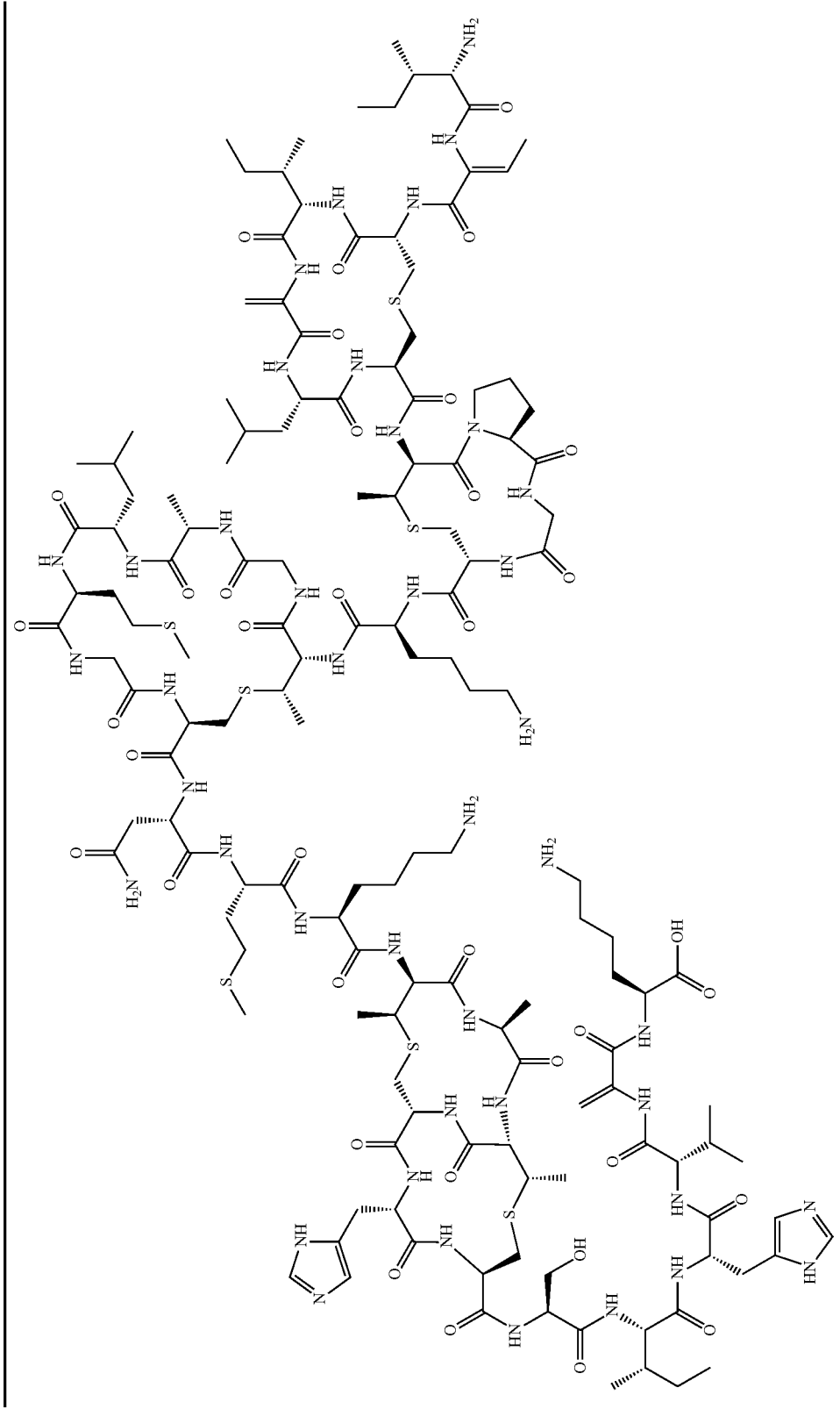
Nisin
Gelatin Polyols of use in this invention generally have at least two nucleophilic centers, e.g., ethylene glycol, hexylene glycol, pentaerythritol, glucose, sorbitol, and 2-aminoethanol.

The range of polyamine or polyol concentration can vary from 0.1% to 5% e.g., 0.2% to 3%, 0.2% to 2%, 0.5% to 2%, and 0.5% to 1%) by weight of the polyurea or polyurethane capsule composition.

By adding excess amount of a cross-linking agent, it has been observed that polyurea/polyurethane formation is driven toward completion thereby reducing the amount of residual polyisocyanate. The reaction stoichiometry requires one amine/hydroxyl group per one isocyanate group. By way of illustration, when combining LUPRANATE M20 (having a molecular weight of 360 and isocyanate functionality of 2.7) and hexamethylenediamine (HMDA; having a molecular weight of 116.21 and amine functionality of 2), the stoichiometry of the system indicates that for each gram of HMDA, 2.23 grams of LUPRANATE is needed. The amount of amine will be in excess if more than one gram of HMDA is used per 2.23 grams of LUPRANATE M20. Using a cross-linker in excess, residual isocyanate amounts are reduced by at least 30%. After the capsules are formed, the free cross-link agent (e.g., hexamethylenediamine, amino-2-methyl-1-propanol, lysine, arginine, and histidine) can be present in the capsule slurry at a concentration of 20 ppm to 2%. The amounts of the residual isocyanate and free cross-linking agent can be removed by washing the capsule slurry with water or carbonate/bicarbonate solution (e.g., sodium carbonate, potassium carbonate, sodium bicarbonate, and potassium bicarbonate).

In one embodiment of the invention, the cross linking agent is added to the capsule reaction at a temperature of 0-55° C. (e.g., 10-50° C. , 15-45° C., 20-40° C., and 22-35° C.).

Chain Termination Agent. Polymerization reactions for forming polyurea/polyurethane capsule wall can be terminated by adding a chain termination agent, e.g., a monofunctional amine or alcohol. Further, a chain termination agent also reacts with isocyanate groups on the surface of the capsules, thus reduced/eliminated isocyanate groups. Examples of a chain termination agent include $C_1$-$C_{20}$ primary and secondary amines, $C_1$-$C_{20}$ alcohols, $C_1$-$C_{20}$ thiols, and any combination thereof.

Capsule Formation Aid. Some capsules useful in the compositions of this invention are prepared in the presence of a capsule formation aid, which can be a surfactant or dispersant. Not to be bound by any theory, capsule formation aids improve the performance of the capsule system. Performance is measured by the intensity of the fragrance release during the pre-rub and post-rub phases. The pre-rub phase is the phase when the capsules have been deposited on the cloth, e.g., after a fabric softener containing capsules has been used during the wash cycle. The post-rub phase is after the capsules have been deposited and the capsules are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and any combination thereof. In general, the range of surfactant concentration in the capsule composition varies from 0.1 to 5% (e.g., 0.5% to 4%, 0.2% to 2%, and 1% to 2%).

Commercially available surfactants include, but are not limited to, sulfonated naphthalene-formaldehyde condensates such as MORWET D425 (sodium salt of naphthalene sulfonate condensate, Akzo Nobel, Fort Worth, Tex.); partially hydrolyzed polyvinyl alcohols such as MOWIOLs, e.g., MOWIOL 3-83 (Air Products; a degree of hydrolysis of 83% and an average molecular weight of 14,000); ethylene oxide-propylene oxide block copolymers or poloxamers such as PLURONIC, SYNPERONIC or PLURACARE materials (BASF); sulfonated polystyrenes such as FLEXAN II (sodium polystyrene sulfonate commercially available from Akzo Nobel); ethylene-maleic anhydride polymers such as ZEMAC series from Vertellus Specialties Inc. (e.g., ZeMac E400, an alternating copolymer of ethylene and maleic anhydride having a average molecular weight of 400,000); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

Processing aids can include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with CMC and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. The amount of surfactant present in the capsule slurry can vary depending on the surfactant used. In some embodiments the amount of surfactant is in the range of 0.05% to 0.2% by weight of the capsule compositions, in particular when CTAC is employed. In another embodiment, the amount of surfactant is in the range of 1% to 3%.

When combined with CMC, a lighter color PVA is preferred. According to the invention, the CMC polymer may be represented by the following structure:

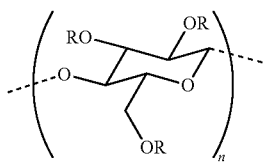

R=H or CH$_2$CO$_2$H

In certain embodiments, the CMC polymer has a molecular weight range between 90,000 Daltons to 1,500,000 Daltons, preferably between 250,000 Daltons to 750,000 Daltons and more preferably between 400,000 Daltons to 750,000 Daltons. The CMC polymer has a degree of substitution between 0.1 to 3, preferably between 0.65 to 1.4, and more preferably between 0.8 to 1.

The carboxymethyl cellulose polymer is present in the capsule slurry at a level from 0.1 to 2% and preferably from 0.3 to 0.7%.

In some embodiments, capsules formed in presence of a capsule aid may unexpectedly provide a perceived fragrance intensity increase of greater than 15%, and preferably an increase of greater than 25% as compared to capsules formed without a capsule formation aid.

Additional Polymers. In addition to the polyisocyanate, cross-linking agent, the encapsulating polymer can also include one or more additional polymers. Additional polymers that can be added to the wall at the formation of the capsules include, e.g., polyamines (polyethylenimine, poly vinyl amines, etc.), polyacrylates and polyquaterniums. In certain embodiments, the additional polymers may be selected from, but is not limited to, amphoteric and cationic polymers having a molecular weight in the range of from 1,000 to 1,000,000, preferably from 10,000 to 500,000, and more preferred between 100,000 to 200,000. Not to be bound by any theory, these additional polymer change the surface property of capsules, improve the stability of the capsules for storage, and/or increase affinity of capsules to treated surface area (e.g., as deposition aids).

Examples of amphoteric and cationic polymers include, but not limited to, polyquaternium and polyvinylamine and its copolymers with vinylformamide and mixtures thereof. Polyquaternium includes polyquaternium-6 (poly(diallyldimethyl-ammonium chloride), commercially available as MERQUAT 100), polyquaternium-47 (a terpolymer of acrylic acid, methacrylamidopropyl trimethylammonium chloride, and methyl acrylate, commercially available as MERQUAT 2001), and polyquaternium-53 (copolymer of acrylic acid, acrylamide, methacrylamidopropyltrimonium chloride, commercially available as MERQUAT 2003PR). Polyvinylamines are polymers which are prepared by acidic or alkaline hydrolysis of poly(N-vinylformamides), as described, e.g., by Gu, et al. ((2002) *J. Appl. Pol. Sci.* 86:3412-3419). The corresponding products are produced in various molecular weights by BASF AG under the trade name "LUPAMIN". These products are used on a large scale, for example, as paper chemicals, in the personal care sector, as super-absorbents or dispersants. The LUPAMIN commercial products still contain the salts formed from the hydrolysis. For the application sector described, the modification of waveguide surfaces, both the salt-containing and the desalinified form can be used. The desalinification can be effected, for example, by ultrafiltration. In a preferred embodiment the polyvinylamine is LUPAMIN 9095 (poly-vinylamine, average molecular weight 340,000 g/mol) commercially available from BASF.

In some embodiments, the encapsulating polymer contains from 0.01 to 20 weight percent of the additional polymer, on a solid basis. In other embodiments, the encapsulating polymer contains from 0.1 to 10 weight percent of the additional polymer, on a solid basis. In particular embodiments, the additional polymer is polyquaternium-6 and is present, on a solid basis, in the range of 0.25 to 10 weight percent. In a further embodiment, the polymer is a mixture of polyquaternium-6 and a polyvinyl amine, specifically LUPAMIN 9095, wherein the polyquaternium-6 may be present, on a solid basis, in the range of preferably 0.5 to 5 weight percent and the polyvinylamine present, on a solid basis, from 0.25 to 10 weight percent. In still a further embodiment, the additional polymer is a mixture of polyquaternium-6 and polyvinylamine wherein the polyquaternium-6 is present, on a solid basis, in the range of preferably 0.5 to 5 weight percent and the polyvinylamine is present, on a solid basis, in the range of preferably 0.5 to 8 weight percent. In yet another embodiment, the additional polymer is a mixture of polyquaternium-6 and polyvinylamine wherein the polyquaternium-6 is present, on a solid basis, at a level of 1.5 weight percent and the polyvinylamine is present, on a solid basis, 1 weight percent.

According to certain other embodiments of the invention, the additional polymer is added at between 35° C. and 55° C.

Catalysts. Catalysts suitable for use in the invention are metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

Core/Active Materials. The core of the capsules of the invention can include one or more active materials including, but not limited to, flavors, fragrance ingredients such as fragrance oils, and/or malodor counteractants. Individual perfume ingredients that can be included in the capsules of this invention include fragrances containing i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxy-octan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2, 2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclodode-catrien-1-ol, 2-isobutyl-4-methyltetrahydro-2H-pyran-4-ol;

x) cycloaliphatic alcohols, such as, for example, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3 a,6,6,9a-tetramethyldodecahydronaphtho[2,1-b]furan, 3a-ethyl-6,6,9a-trimethyldodecahydro-naphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetra-methylcyclohexanone, 4-tert.-pentylcyclohexanone, 5-cyclohexadecen-1-one, 6,7-di-hydro-1,1,2,3,3-pentamethyl-4(5H)-indanone, 5-cyclohexadecen-1-one, 8-cyclohexa-decen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexa-hydro-5or 6-indenyl acetate, 4,7-methano-3a,4,5,6,7,7a-hexahydro-5 or 6-indenyl propionate, 4,7-methano-3a,4,5,6,7,7a-hexa-hydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)-propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethyl-phenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno [1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-iso-propylphenyl)propanal, 2-methyl-3-(4-tert.-butylphenyl)propanal, 3-(4-tert.-butyl-phenyl)propanal, cinnamaldehyde, alpha-butylcinnamaldehyde, alpha-amylcinnam-aldehyde, alpha-hexylcinnamaldehyde, 3-methyl-5-phenylpentanal, 4-methoxy-benzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6', 8',8'-hexamethyl-2-aceto-naphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophen-one, cinnamonitrile, 5-phenyl-3-methyl-2-pentenonitrile, 5-phenyl-3-methylpentano-nitrile, methyl anthranilate, methy-N-methylanthranilate, Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde, 6-isopropylquinoline, 6-iso-butylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1, 16-olide, 10-oxa-1,16-hexadecanolide, 11-oxa-1,16-hexadecanolide, 12-oxa-1,16-hexade-canolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated active material is from 0.5% to 80% (e.g., 5 to 65%, 15 to 55%, 20 to 45%, and 25 to 40%) by weight of the capsule slurry as prepared; and the amount of the capsule wall is from 0.5% to 25% (e.g., 1.5 to 15% and 2.5 to 10%) also by weight of the capsule slurry as prepared. In other embodiments, the amount of the encapsulated active material is from 15% to 99.5% (e.g., 50 to 98% and 30 to 95%) by weight of the capsule, and the amount of the capsule wall is from 0.5% to 85% (e.g., 2 to 50% and 5 to 70%) by weight of the capsule.

Core Modifiers. In addition to the fragrance materials, the present invention also contemplates the incorporation of other core modifiers including solvents, emollients, and particles or polymeric core modifiers into the oil core.

Suitable solvents can be hydrophobic materials that are miscible in the active materials. The solvent materials serve to increase the compatibility of various active materials, increase the overall hydrophobicity of the mixture containing the active materials, influence the vapor pressure, or serve to structure the mixture. Useful solvents include those having reasonable affinity for the active materials and a ClogP greater than 2.5, preferably greater than 3.5 and more preferably greater than 5.5. In some embodiments, the solvent is combined with the active materials that have ClogP values as set forth above. It should be noted that selecting a solvent and active material with high affinity for each other will result in improvement in stability. Suitable solvents include triglyceride oil, mono and diglycerides, mineral oil, silicone oil, diethyl phthalate, polyalpha olefins, castor oil, isopropyl myristate, mono-, di- and tri-esters and mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., R2CO—[OCH$_2$—CH(OCOR1)-CH$_2$O—]$_n$, where R1 and R2 can be H or $C_4$-$C_{26}$ aliphatic chains, or mixtures thereof, and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBIL PURESYN esters; mineral oil; silicone oils such polydimethyl siloxane and polydimethyl-cyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

While no solvent is needed in the oil core, it is preferable that the level of solvent in the core of the capsule product is 80 wt % or less, preferably 50 wt % or less (e.g., 0-20 wt % and 0.5-15 wt %).

When the active material is a fragrance, it is preferred that fragrance ingredients within a fragrance having a ClogP of 0.5 to 15 are employed. For instance, the ingredients having a ClogP value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance. Those skilled in the art will appreciate that many fragrances can be created employing various solvents and fragrance ingredients. The use of relatively low to intermediate ClogP fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high logP materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL 8202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and even more preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

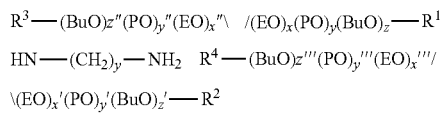

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

One or more adjunct materials may be added to the capsule compositions in the amount of from 0.01% to 25% (e.g., from 0.5% to 10%).

The adjunct material can be a solubility modifier, an antibacterial, a sunscreen active, an antioxidant, a malodor counteracting agent, a density modifier, a stabilizer, a viscosity modifier, a pH modifier, or any combination thereof. These modifiers can be present in the wall or core of the capsules, or outside the capsules in compositions of this invention. Preferably, they are in the core as a core modifier.

Nonlimiting examples of a solubility modifier include surfactants (e.g., SLS and Tween 80), acidic compounds (e g , mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, secondary, or tertiary amines, and primary, secondary, or tertiary alkanolamines), ethyl alcohol, glycerol, glucose, galactose, inositol, mannitol, glactitol, adonitol, arabitol, and amino acids.

Exemplary antibacterials include bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2 hydroxy-diphenylether), thymol, and triclocarban.

Suitable sunscreen actives include oxybenzone, octyl-methoxy cinnamate, butylmethoxy dibenzoyln ethane, p-aminobenzoic acid and octyl dimethyl-p-aminobenzoic acid.

Examples of antioxidants include beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase.

Malodor counteracting agents include, but not limited to, an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, and zinc undecenylate. More suitable malodor counteracting agents are polymers containing an α-keto, benzaldehyde, or α,β-unsaturated carbonyl moiety, such as those described in US Application Publications 2012/0294821, 2013/0101544 and 2013/0101545.

The density of the capsule slurry and/or the oil core can be adjusted so that the capsule composition has a substantially uniform distribution of the capsules using known density modifiers or technologies such as those described in Patent Application Publications WO 2000/059616, EP 1 502 646, and EP 2 204 155. Suitable density modifiers include hydrophobic materials and materials having a desired molecular weight (e.g., higher than 12,000), such as silicone oils, petrolatums, vegetable oils, especially sunflower oil and rapeseed oil, and hydrophobic solvents having a desired density (e.g., less than 1,000 Kg/m³ at 25° C., such as limonene and octane.

In some embodiments, a stabilizer (e.g., a colloidal stabilizer) is added to a capsule composition to stabilize the emulsion and/or capsule slurry. Examples of colloidal stabilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid.

Viscosity control agents (e.g., suspending agents), which may be polymeric or colloidal (e.g., modified cellulose polymers such as methylcellulose, hydoxyethylcellulose, hydrophobically modified hydroxyethylcellulose, and crosslinked acrylate polymers such as Carbomer, hydrophobically modified polyethers) can be included in the capsule composition, in the capsule core or wall, or in the capsule slurry outside the capsules. Optionally, silicas, either hydrophobic or hydrophilic, can be included at a concentration from 0.01 to 20%, more preferable from 0.5 to 5%, by the weight of the capsule composition. Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPERNAT 22S, SIPERNAT 50S (available from Degussa), and SYLOID 244 (available from Grace Davison).

One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like.

Further suitable humectants, as well as viscosity control/suspending agents, are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. No. 5,500,223 and 6,608,017.

In some embodiments, one or more pH modifiers are included in the capsule composition to adjust the pH value of the capsule slurry and/or the capsule cores. The pH modifiers can also assist in the formation of capsule walls by changing the reaction rate of the crosslinking reactions that form the capsule walls. Exemplary pH modifiers include metal hydroxides (e.g., LiOH, NaOH, KOH, and $Mg(OH)_2$), metal carbonates and bicarbonates ($CsCO_3$ $Li_2CO_3$, $K_2CO_3$, $NaHCO_3$, and $CaCO_3$), metal phosphates/hydrogen phosphates/dihydrogen phosphates, metal sulfates, ammonia, mineral acids (HCl, $H_2SO_4$, $H_3PO_4$, and $HNO_3$), carboxylic acids (e.g., acetic acid, citric acid, lactic acid, benzoic acid, and sulfonic acids), and amino acids.

The capsule compositions of this invention can also include one or more non-confined unencapsulated active materials from 0.01 to 50%, more preferably from 5 to 40%.

The level of solvent materials, particles, adjuncts, or core modifiers can be greater than 10% (e.g., greater than 30% and greater than 70%). In addition to the solvent, it is preferred that a fragrance having a weight-averaged ClogP of 2.5 and greater (e.g., 3 or greater, 2.5 to 7, and 2.5 to 5) is employed. The weight-averaged ClogP is calculated as follows:

ClogP={Sum[(Wi)(ClogP)i]}/{Sum Wi}

In which Wi is the weight fraction of each fragrance ingredient and (ClogP)i is the ClogP of that fragrance ingredient.

As an illustration, it is preferred that greater than 60 weight percent, preferably greater than 80 and more preferably greater than 90 weight percent of the fragrance chemicals have ClogP values of greater than 3.3, preferably greater than 4 and even more preferably greater than 4.5. Those with skill in the art will appreciate that many formulations can be created employing various solvents and fragrance chemicals. The use of a high level of high ClogP fragrance chemicals will likely require a lower level of hydrophobic solvent than fragrance chemicals with lower ClogP to achieve similar performance stability. As those with skill in the art will appreciate, in a highly preferred embodiment, high ClogP fragrance chemicals and hydrophobic solvents comprise greater than 80, preferably more than 90 and even more preferably greater than 95 weight percent of the fragrance composition. As discussed above, specific ClogP values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

In addition to the capsules and adjunct materials described above, the capsule composition of this invention can contain one or more other delivery compositions such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof.

Deposition Aids. Deposition aids can also be used to assist the deposition of capsules to surfaces such as fabric, hair or skin. Examples include but are not limited to anionically, cationically, nonionically, or zwitterionically charged water-soluble polymers which can be added to polyurea or polyurethane capsules. These water-soluble polymers can also be amphoteric polymers with a ratio of cationic and anionic functionalities resulting in a net total charge of zero or positive, i.e., cationic. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from 1,000 to 1000,000,000, preferably from 5,000 to 10,000,000. As used herein, molecular weight is provided as weight average molecular weight.

Particular examples of cationic polymers that can be used to coat the polyurea or polyurethane capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDAD-MAC on cellulose, e.g., CELQUAT L-200 (POLY-QUATERNIUM-4), POLYQUATERNIUM-10 and POLY-QUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

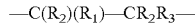

wherein, $R_1$ is any alkane from C1-C25 or H, wherein the number of double bonds ranges from 0-5, $R_1$ is an alkoxylated fatty alcohol with any alkoxy carbon-length of C1-C25, or $R_1$ is a liquid crystalline moiety that can provide the polymer with thermotropic liquid crystalline properties $R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

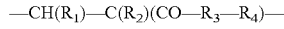

wherein, $R_1$ is any alkane from C1-C25 or H with number of double bonds from 0-5, $R_1$ is an alkoxylated fatty alcohol with a C1-C25 alkyl chain length, or $R_1$ is a liquid crystalline moiety that provides the polymer with thermotropic liquid crystalline properties;

$R_2$ is H or $CH_3$;

$R_3$ is a C1-25 alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAF-QUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: —[N(CH$_3$)$_2$—(CH$_2$)$_x$—NH—(CO)—NH-(CH$_2$)$_y$—N(CH$_3$)$_2$)—(CH$_2$)$_z$—O—(—CH$_2$)$_p$]$_n$—, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si(R$_1$)(R$_2$)—O—]$_x$—[Si(R$_3$)(R$_2$)—O—]$_y$,— where $R_1$ is any alkane from C1-C25 or H with number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be —$R_1$—$R_4$, where $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, —COOH, —COO— alkali salt, any C1-25 alcohol, —C(O)—$NH_2$ (amide), —C(O)—N(R$_2$)(R$_2$')(R$_2$''), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be —(CH$_2$)$_x$—O—CH$_2$—CH(OH)—CH$_2$—N(CH$_3$)$_2$—CH$_2$—COOH and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) Ind. Eng. Chem. Fundam. 25:120-125.

As indicated, the addition of hydrophobic polymers to the core can also improve stability by slowing diffusion of the fragrance from the core. The level of polymer is normally less than 80% of the core by weight, preferably less than 50%, and even more preferably less than 20%. The basic requirement for the polymer is that it be miscible or compatible with the other components of the core, namely the fragrance and other solvent. Preferably, the polymer also thickens or gels the core, thus further reducing diffusion.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

In certain embodiments of the invention, the capsule slurry is cured at a temperature greater than 55° C.; greater than 65° C.; greater than 75° C.; greater than 85° C.; greater than 95° C.; greater than 105° C. or greater than 120° C.

Capsules prepared in accordance with this invention preferably have a size in the range of from 0.01 to 1000 microns (e.g., 0.5 to 1000 microns, 1 to 200 microns, 0.5 to 150 microns, 2 to 50 microns, 5 to 25 microns, and 2 to 15 microns). The capsule distribution can be narrow, broad, or multi-modal.

In some embodiments, capsules are purified before use. Purification can be achieved by washing with water or an aqueous solution, diafiltration, and centrifugation.

Suitable diafiltration processes are those described in US Patent Application Publication 2014/0134242 and Sheth et al., J. of Membr. Sci. 2003, 211.2, 251-61. The capsule slurry can also be washed with water until a neutral pH in the capsule slurry is achieved. For the purposes of the present invention, the capsule compositions can be washed using any conventional method including the use of a separatory funnel, filter paper, centrifugation and the like. The capsule suspension can be washed one, two, three, four, five, six, seven, eight, nine, ten or more times until a neutral pH, i.e., pH 7±0.5, is achieved. The pH of the purified capsules can be determined using any conventional method including, but not limited to pH paper, pH indicators, or a pH meter.

A capsule suspension of this invention is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium carbonate, sodium bicarbonate, sodium chloride, potassium carbonate, potassium bicarbonate, potassium chloride, and bi-sulphite salts.

Stabilizing Agents. The capsule compositions of this invention each contain one or more stabilizing agents to improve the stability for an extended period of storage. When one of these capsule compositions is added to a consumer product such as a liquid fabric softener/freshener and liquid detergent, this composition will also improve the viscosity stability of the consumer product, thus extend the shelf life of the product.

The stabilizing agent in the capsule composition can be present in an amount effective to stabilize the composition and/or the final consumer product containing the composition. This amount can be 1 ppm or greater (e.g., 20 ppm or greater, 20 ppm to 20%, 50 ppm to 10%, 50 ppm to 2%, 50 ppm to 1%, 50 to 2000 ppm, and 50 to 1000 ppm). Its concentration in a consumer product can be 20 ppm to 2% (e.g., 50 ppm to 2%, 50 ppm to 1%, 50 to 2000 ppm, and 50 to 1000 ppm).

Useful stabilizing agents include multi-functional amines, amino acids/peptides, mono-functional amines, polymers, and a polymeric mixture. These stabilizing agents are in presence in the compositions as free compounds, which are not covalently attached to the capsule walls, being part of the capsule walls, or encapsulated in capsules.

Multi-functional amines are those having at least an amine group (primary, secondary, or tertiary) and one or more other functional groups such as an amine and hydroxyl group. Exemplary multi-functional amines include hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, amino-2-methyl-1-propanol branched polyethylenimine, chitosan, 1,3-diamino-guanidine, 1,1-dimethylbiguanide, and guanidine. Suitable amino acids/peptides include arginine, lysine, histidine, ornithine, nisin, and gelatin. Suitable stabilizing polymers include polyvinylpyrrolidone, polyvinylpyridine-N-oxide, and polyvinyl imidazolinium. These polymers sometimes are used in combination with a second polymer (e.g., a block copolymer) such that the second polymer.

Monofunational amines have a single amine group. Examples include $C_1$-$C_{20}$ primary, secondary, or tertiary amines, each of which typically has a molecular weight of 30 to 800 Daltons (e.g., 31 to 500 Daltons and 31 to 300 Daltons). They can be linear, branched, cyclic, acyclic, saturated, unsaturated, aliphatic, and/or aromatic. Nonlimiting examples are methylamine, dimethylamine, trimethylamine, ethylamine, diethylamine, triethylamine, propylamine, isopropylamine, butylamine, dodecylamine, tetradecylamine, aniline, 4-methylaniline, 2-nitroaniline, diphenyl amine, pyrrolidone, piperidine, and morpholine.

Fabric Conditioning Agents. The capsule compositions of this invention are suitable for use in personal care products, fabric care products, and home care products.

More specifically, the capsule compositions are suitable for preparing perfumed liquid fabric softeners/fresheners. It is discovered that these capsule compositions unexpectedly improve the viscosity stability of liquid fabric softeners.

At least one fabric softening agent is present in each liquid fabric softener, preferably at a concentration of 1 to 30% (e.g., 4 to 20%, 4 to 10%, and 8 to 15%). It would be obvious to a skilled person in the art to determine the concentration of a fabric softening agent while keeping its conditioning benefits and also maintaining a reasonable stability and shelf life. In addition, the ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

Applications. The capsule compositions of the present invention are well-suited for use in personal care products including, without limitation, deodorants and antiperspirants, shampoos, hair conditioners, hair rinses, hair refreshers, hair styling products, hair combing creams, body washes such as shower gels, body locations, body sprays, antiperspirants, deodorants, soaps products and the like. In particular embodiments, the compositions are of use in an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant.

The capsule compositions are also well-suited for use in fabric care products such as rinse conditioners, fabric liquid conditioners, tumble drier sheets, fabric refresher sprays, ironing liquids, and liquid and powder detergents including unit dose tablets and capsules, scent boosters; home care products such as all-purpose cleaners including bathroom cleaners; bath tissues; rug deodorizers; candles; room deodorizers; floor cleaners; disinfectants; window cleaner; and fabric refreshers; personal hygiene products such as hand sanitizers; toiletries; and oral care products such as tooth powder.

Further, the capsule compositions are useful in the following products: (a) household devices including paper towels, disposable wipes, room deodorizers, and fabric softener dryer sheets, (b) baby care products such as diaper rash cream/balm and baby powder, (c) baby care devices, e.g., diapers, bibs, and wipes, (d) health care products including tooth paste, oral rinse, tooth whiteners, denture adhesive, hand sanitizer, and antiinflammatory balms, ointment or spray, (e) health care devices, e.g., dental floss, toothbrushes, feminine hygiene products such as tampons, feminine napkins and wipes, and pantiliners; (f) personal care products including personal cleansers (bar soap, body wash), sunscreen (spray or lotion), wax-based deodorant, glycol/soap type deodorant, lotion, body powder, shave cream, bath soak, exfoliating scrub, (g) personal care devices such as facial tissues and cleansing wipes, (h) hair care products including shampoo (liquid and dry powder), hair conditioner (rinse out and leave-in), hair fixative and styling aids, hair bleaches, dyes and colorants, and (i) beauty care like fine fragrance (See, e.g., U.S. Pat. No. 4,428,869), solid perfume, liquid foundation, powder foundation, eye shadow, lipstick/lip balm.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Patent Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The invention is described in greater detail by the following non-limiting examples.

EXAMPLE 1

A capsule composition of this invention, i.e., Eden PU, was prepared following the procedure described below. Also see U.S. Pat. No. 8,299,011.

A fragrance emulsion was first prepared by mixing 96 g of a fragrance, Eden (International Flavors and Fragrance, Union Beach, N.J.), 24 g of NEOBEE oil (Stepan, Chicago, Ill.) and 9.6 g of isocyanate monomer, Lupranate®M20 (BASF corporation, Wyandotte, Mich., USA) to form an oil phase. In a separate beaker, a 3% surfactant solution (160 g) was prepared by dissolving 4.8 g of Morwet D-425 (Akzo Nobel, Fort Worth, Tex., USA) in water. The oil phase was then emulsified into the surfactant solution to form a fragrance emulsion under shearing (Ultra Turrax®, T25 Basic, IKA® WERKE) at 6500 rpm for two minutes.

To the fragrance emulsion thus prepared was added 10.8 g of 40% hexamethylenediamine (HMDA) (INVISTA, Wichita, Kans., USA) under constant mixing with an overhead mixer. Formation of polyurea ("PU") capsule was immediately visible by optical microscopy. The mixer speed was reduced after the addition of HMDA was complete. The capsule slurry was cured at 55° C. for 2 hours to obtain Capsule Composition Eden PU.

Eden PU thus prepared typically contains 0.4 to 1% free HMDA, which can be measured by Liquid chromatography-mass spectrometry (LC-MS) or Gas chromatography (GC).

EXAMPLE 2

A fabric softener of this invention, i.e., Sample 1, was prepared using Capsule Composition Eden PU.
Sample 1 of This Invention Sample 1 contains an unfragranced fabric softener base, 0.9% of a fragrance oil, 0.2% neat oil equivalent ("NOE") of Eden PU, and 0.2% NOE of a poly(melamine-formaldehyde) ("MF") capsule. The fabric softener base, commercially available from Unilever under the brand name Comfort, has 10.5% of a fabric softening agent. The fragrance oil is commercially available from International Flavors and Fragrances under the name Rising Legend. And the MF capsule is Thunder C20, commercially available also from International Flavors and Fragrances.

To prepare Sample 1, the following ingredients were mixed until homogeneous: 977.6 g of unfragranced softener base, 9 g of Rising Legend, 7.14 g of Thunder C20, and 6.25 g of Eden PU.
Comparative Sample For comparison, a comparative fabric softener, i.e., Comparative 1', was also prepared using the same ingredients as Sample 1 except that 7.14 g of Eden C25 (a MF capsule commercially available from International Flavors and Fragrances) was used instead of Eden PU.
Viscosity Stability Evaluation Sample 1 and Comparative 1' were evaluated for their viscosity stabilities stored at 37° C. and 40° C. for 4, 8, and 12 weeks.

Each viscosity was measured on a Physica ASC32-MCR300 with a concentric cylinder CC27 (DIN 53019) at a constant shear rate of 20 second$^{-1}$ for a period of 3 minutes under 25° C.

The viscosity results are shown in Table 1 below.

TABLE 1

| | | Viscosity (mPas) at 20 second$^{-1}$ | | | | | |
|---|---|---|---|---|---|---|---|
| | | 4 weeks | | 8 weeks | | 12 weeks | |
| Fabric Softener | initial | 37° C. | 40° C. | 37° C. | 40° C. | 37° C. | 40° C. |
| Sample 1 | 42 | 39 | 54 | 38 | 55 | 40 | 69 |
| Comparative 1' | 45 | 73 | 128 | 77 | 162 | 89 | 220 |

Unexpectedly, Sample 1 containing stabilizing agent HMDA has a much greater viscosity stability than Comparative 1' without a stabilizing agent during the extended period of storage at the two temperatures in this evaluation.

EXAMPLE 3

A second capsule composition of this invention, i.e., LL Cloud PU, was prepared following the same procedure described in Example 1 above except that fragrance LL Cloud (commercially available from International Flavors and Fragrance, Union Beach, N.J.), instead of Eden, was used.

Capsule Composition LL Cloud PU thus prepared typically contains 0.4 to 1% free HMDA, which can be measured by an instrument such as LC/MS and GC.

EXAMPLE 4

A fabric softener of this invention, i.e., Sample 2, was prepared using Capsule Composition LL Cloud PU.
Sample 2

Sample 2 contains an unfragranced model fabric softener base, 0.76% of a fragrance oil, 0.3% NOE of LL Cloud PU.

The unfragranced model fabric softener has 12% esterquat (Rewoquat WE18, a fabric softening agent commercially available from Evonik). The fragrance oil is Spring Equinox commercially available from International Flavors and Fragrances.
Comparative 2'

For comparison, a comparative fabric softener, i.e., Comparative 2', was also prepared using the same ingredients as Sample 2 except that 0.3% NOE Jillz C20V12 (a MF capsule commercially available from International Flavors and Fragrances) was used instead of LL Cloud PU.

Viscosity Stability Evaluation

Sample 2 and Comparative 2', along with the unfragranced model fabric softener, were evaluated for their viscosity stabilities stored at 37° C. and 40° C. for 4, 8, and 12 weeks following the same procedure described in Example 2 above.

The viscosity results are shown in Table 2 below.

TABLE 2

| | | Viscosity (mPas) at 20 second$^{-1}$ | | | | | |
|---|---|---|---|---|---|---|---|
| | | 4 Weeks | | 8 Weeks | | 12 Weeks | |
| Fabric Softener | initial | 37° C. | 40° C. | 37° C. | 40° C. | 37° C. | 40° C. |
| Sample 2 | 57 | 49 | 50 | 44 | 49 | 46 | 61 |
| Model Softener | 56 | 58 | 70 | 66 | 68 | 73 | 138 |
| Comparative 2' | 87 | 79 | 92 | 75 | 95 | 70 | 122 |

Unexpectedly, Sample 2 containing stabilizing agent HMDA has a much greater viscosity stability than the model softener and Comparative 2', both of which do not contain a stabilizing agent.

EXAMPLE 5

A third fabric conditioning composition of this invention, i.e., Sample 3, was prepared using Capsule Composition Greenfields PU described below.

Greenfields PU was prepared following the same procedure for Eden PU described in Example 1 except that fragrance Greenfields (commercially available from International Flavors and Fragrance, Union Beach, N.J.), instead of Eden, was used.

Capsule Composition Greenfields PU thus prepared typically contains 0.4 to 1% free HMDA, which can be measured by an instrument such as LC/MS and GC.

Sample 3 of this invention contains 0.6% NOE of Greenfields PU and an unfragranced model fabric softener base having 20% of a fabric conditioning agent and.
Comparative 3'

For comparison, a comparative fabric softener, i.e., Comparative 3', was also prepared using the same ingredients as Sample 3 except that 0.6% NOE Greenfields C20V12 (a MF capsule commercially available from International Flavors and Fragrances) was used instead of Greenfields PU.

Viscosity Stability Evaluation

Sample 3 and Comparative 3', along with the unfragranced model fabric softener, were evaluated for their viscosity stabilities stored at 37° C. for 4 and 8 weeks following the same procedure described in Example 1 above.

The viscosity results are shown in Table 3 below.

TABLE 3

| Compositions | Viscosity (mPa · s) at 20 second$^{-1}$ | | |
|---|---|---|---|
| Sample 3 | 90 | 99 | 163 |
| Unfragranced | 80 | 102 | 272 |
| Comparative 3' | 98 | 129 | 219 |

Unexpectedly, Sample 3 containing stabilizing agent HMDA has a much greater viscosity stability than the unfragranced model conditioning composition and Comparative 3', both of which do not contain a stabilizing agent.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing a stable capsule composition, one skilled in the art can prepare suitable capsules use different polyisocyanates, cross-linking agents, and/or capsule formation aids, varying the concentrations of these wall-forming materials and/or catalysts to achieve desirable organoleptic or release profiles in a consumable product. Further, the ratios among polyisocyanates, cross-linking agents, capsule forming aids, adjuvents, core modifiers, active materials, and catalysts can also be determined by a skilled artisan through assays known in the art to prepare capsule compositions with desirable properties. A skilled person can also choose a suitable stabilizing agent and determine its concentration in a capsule composition and final product.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A capsule composition comprising:
   a capsule that has an oil core containing an active material and a capsule wall encapsulating the oil core, and
   a stabilizing agent,
wherein the active material is a fragrance, a flavor, a malodor counteractant, or a combination thereof; the wall is formed of polyurea; the stabilizing agent, being 20 ppm to 2000 ppm by the weight of the capsule composition, is free hexamethylene diamine; the polyurea is a reaction product of a polyfunctional isocyanate and a polyfunctional amine as a cross-linking agent in the presence of a capsule formation aid; the capsule wall is 2 to 50% by weight of the capsule; and the oil core is 50 to 98% by weight of the capsule.

2. The capsule composition of claim 1, wherein the polyfunctional isocyanate is an aromatic polyfunctional isocyanate, aliphatic polyfunctional isocyanate, or combination thereof, the aromatic polyfunctional isocyanate containing a phenyl, tolyl, xylyl, naphthyl, or diphenyl moiety, or a combination thereof and the aliphatic polyfunctional isocyanate being a trimer of hexamethylene diisocyanate, a trimer of isophorone diisocyanate, a biuret of hexamethylene diisocyanate, or a combination thereof.

3. The capsule composition of claim 2, wherein the polyfunctional isocyanate is an aromatic polyfunctional isocyanate selected from the group consisting of polyisocyanurates of toluene diisocyanate, trimethylol propane-adducts of toluene diisocyanate, and trimethylol propane-adducts of xylylene diisocyanate.

4. The capsule composition of claim 2, wherein the polyfunctional isocyanate is an aliphatic polyfunctional isocyanate selected from the group consisting of dimers, biurets, symmetric trimers, asymmetric trimers of hexamethylene diisocyanate.

5. The capsule composition of claim 1, wherein the polyfunctional amine is hexamethylene diamine, hexaethylenediamine, ethylenediamine, 1,3- diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, or a combination thereof.

6. The capsule composition of claim 5, wherein the cross-linking agent is hexamethylene diamine, hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

7. The capsule composition of claim 6, wherein the polyfunctional isocyanate is polymeric methylene diphenyl diisocyanate.

8. The capsule composition of claim 1, wherein the capsule formation aid is a polyvinyl alcohol, polystyrene sulfonate, carboxymethyl cellulose, naphthalene sulfonate, polyvinylpyrrolidone, copolymer of vinyl pyrrolidone and quaternized dimethylaminoethyl methacrylate, or mixture thereof.

9. The capsule composition of claim 1, wherein the stabilizing agent is hexamethylene diamine, hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

10. The capsule composition of claim 1, wherein the active material is a fragrance.

11. The capsule composition of claim 10, wherein the capsule wall is formed of polyurea that is a reaction product between a polyfunctional isocyanate and a polyfunctional amine in the presence of a capsule formation aid, the polyfunctional isocyanate is polymeric methylene diphenyl diisocyanate, hydrogenated polymeric methylene diphenyl diisocyanate, methylene diphenyl diisocyanate, hydrogenated methylene diphenyl diisocyanate, a polyisocyanate based on xylene diisocyanate, or a polyisocyanate based on toluene diisocyanate, the polyfunctional amine is hexamethylenediamine, polyethylenimine, guanidine, arginine, lysine, or histidine, and the capsule formation aid is naphthalene sulfonate condensate or a salt thereof.

12. The capsule composition of claim 1, further comprising a deposition aid that is an anionic, cationic, nonionic or zwitterionic polymer.

13. The capsule composition of claim 12, wherein the deposition aid is polyquaternium-6, polyquaternium-47, polyquaternium-53, polyvinylamine, poly(vinylamine-co-vinylformamide), or a combination thereof.

14. The capsule composition of claim 1, wherein the capsule, before formulating into the capsule composition, is purified by washing the capsule with water or an aqueous solution.

15. The capsule composition of claim 1, wherein the capsule, before formulating into the capsule composition, is cured at a temperature of 55° C. or greater.

16. A consumer product comprising a capsule composition of claim 1.

17. The consumer product of claim 16, wherein the consumer product is a shampoo, a hair conditioner, a soap, a body wash, a cosmetic preparation, an all-purpose cleaner, a fabric softener, a fabric refresher, an ironing water, a fabric detergent, a unit dose tablet or capsule, a scent booster, a drier sheet, a fine fragrance, an Eau De Toilette product, a deodorant, an anti-perspirant, an roll-on product, or an aerosol product.

18. The consumer product of claim 17, wherein the consumer product is a fabric softener containing 1 to 30% of a fabric softening agent, and 0.1 to 30% of the capsule.

19. The consumer product of claim 18, wherein the fabric softener contains 2 to 25% of a fabric softening agent.

20. The consumer product of claim 19, wherein the fabric softener contains 50 to 2000 ppm of hexamethylenediamine as the stabilizing agent.

* * * * *